US010579777B2

(12) United States Patent
Ziavras et al.

(10) Patent No.: US 10,579,777 B2
(45) Date of Patent: Mar. 3, 2020

(54) STRUCTURAL HEALTH MONITORING SYSTEM AND ASSOCIATED METHODS

(71) Applicant: New Jersey Institute of Technology, Newark, NJ (US)

(72) Inventors: Sotirios Ziavras, Fort Lee, NJ (US); William Contreras, Nutley, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 764 days.

(21) Appl. No.: 15/299,105

(22) Filed: Oct. 20, 2016

(65) Prior Publication Data

US 2017/0116383 A1    Apr. 27, 2017

Related U.S. Application Data

(60) Provisional application No. 62/422,685, filed on Oct. 21, 2015.

(51) Int. Cl.
*G06F 19/00* (2018.01)
*G06F 17/30* (2006.01)

(52) U.S. Cl.
CPC ............................... *G06F 19/3418* (2013.01)

(58) Field of Classification Search
CPC ..... A61K 33/00; A61M 16/10; A61M 16/122; A61M 2016/1025; A61M 2202/0007; A61M 2202/0078; A61M 2202/0275; A61M 2205/07; A61M 2205/12; A62B 7/08; B01J 12/007; C01B 21/24; G06F 19/3418
USPC ..... 702/56, 182, 183, 185, 187, 188, 34, 35, 702/179
See application file for complete search history.

(56) References Cited

U.S. PATENT DOCUMENTS

| 7,925,455 B2 * | 4/2011 | Pado ............... G01N 29/043 702/36 |
| 2007/0055476 A1 * | 3/2007 | Whisnant ............ G05B 9/02 702/179 |
| 2007/0260425 A1 * | 11/2007 | Kim ................. G01H 9/004 702/182 |

OTHER PUBLICATIONS

Lynch, et al., Embedding Damage Detection algorithms in a Wireless Sensing Unit for Operational Power Efficiency, Smart Materials and Structures, 2004, 13, (4).
Gorinevsky, et al., Spatio-Temporal Filter for Structural Health Monitoring, American Control Conference, 2006.
Serker, et al., A Non-Physics-Based Approach for Vibration-Based Structural Health Monitoring Under Changing Environmental Conditions, Structural Health Monitoring, 2010, 9, (2), pp. 145-158.
Bocca, et al., Structural Health monitoring in Wireless Sensor Networks by the Embedded Goertzel Algorithm, IEEE/ACM International Conference on Cyber-Physical Systems, 2011.

(Continued)

*Primary Examiner* — John H Le
(74) *Attorney, Agent, or Firm* — McCarter & English, LLP

(57) ABSTRACT

Exemplary embodiments of the present disclosure relate to systems and methods for structural health monitoring in which a sensor network includes motes distributed with respect to a structure. The sensor network can utilize dynamic pattern matching to monitor and localize damage in the structure without modeling or solving equations of the engineered structure, and without ascertaining or separately accounting for extraneous and often-difficult-to-recognize or evaluate factors, such as of the environmental and stimuli-related variability type.

14 Claims, 11 Drawing Sheets

(56) References Cited

OTHER PUBLICATIONS

Gonzalez, et al., Vibration-Based Statistical Damage Detection for Scale Wind Turbine Blades Under Varying Environmental Conditions, Surveillance 7, 2013.

Jin et al., Vibration-Based Structural Health Monitoring Using Adaptive Statistical Method Under Varying Environmental Condition, Proceedings of SPIE, vol. 9064, 2014.

* cited by examiner

STRUCTURAL HEALTH MONITORING SYSTEM AND ASSOCIATED METHODS

CROSS-REFERENCE TO RELATED APPLICATION

The present application claims priority benefit to U.S. Provisional Patent Application No. 62/244,685, entitled "Wireless Sensor Network," which was filed on Oct. 21, 2015. The entire content of the foregoing provisional application is incorporated herein by reference.

TECHNICAL FIELD

The present disclosure is directed to sensor systems and methods for monitoring the integrity of physical structures.

BACKGROUND

Much research has been done regarding the use of wireless sensor networks (WSNs) for structural health monitoring (SHM) on engineering structures. Most commonly, SHM is performed by analyzing structural vibrations. The problem with using vibrations for SHM is that vibrations can be affected by many factors, not just the condition of the structure (factors other than structural condition will herein be referred to as 'extraneous factors'). Environmental factors such as temperature and humidity are examples of extraneous factors, as are factors related to the stimuli that produce the vibrations being monitored (e.g., the magnitude and placement of the stimuli affect the vibrations). These factors all contribute to the vibrations making it difficult to determine the contribution of structural condition to the vibrations.

The problem of environmental and operational variability associated with SHM based on vibrations has received a good amount of attention in research. Generally, approaches to the problem can be divided into two main categories: input-output and output-only sensor networks. With input-output approaches, in determining structural condition, measured values of extraneous parameters are input to regression models that describe the relationship between structural response and extraneous parameters. The disadvantage of this approach is that it is often difficult to establish good regression models. With output-only approaches, statistical methods are used to determine structural condition without measuring the extraneous factors.

Many different output-only methods have been proposed. One technique that has been investigated is the usage of factor analysis. Another popular approach is the usage of principal component analysis (PCA). González, A. G. and Fassois, S. D.: '*Vibration-Based Statistical Damage Detection for Scale Wind Turbine Blades under Varying Environmental Conditions*', in, Surveillance 7, 2013, use PCA to perform SHM on wind turbines. Jin, S.-S. and Jung, H.-J.: '*Vibration-Based Structural Health Monitoring Using Adaptive Statistical Method under Varying Environmental Condition*', in, Proceedings of SPIE Vol. 9064, 2014, use adaptive PCA to continually update the PCA model with new data to improve the performance of the system. Kamrujjaman Serker, N. H. M., Wu, Z., and Li, S.: '*A Nonphysics-Based Approach for Vibration-Based Structural Health Monitoring under Changing Environmental Conditions*', Structural Health Monitoring, 2010, 9, (2), pp. 145-158, propose an output-only method involving regression analysis to compensate for environmental and operational variability. Gorinevsky, D. and Gordon, G.: '*Spatio-Temporal Filter for Structural Health Monitoring*', in, American Control Conference, 2006, suggest using a spatio-temporal infinite impulse response to filter out the environmental and operational effects from damage estimates. Overall, these approaches are promising with regard to achieving immunity to environmental and stimuli-related variability but they tend to be computationally intensive.

More efficient output-only methods suitable for implementation in WSNs have also been proposed. Bocca, M., Toivola, J., Eriksson, L. M., et al.: '*Structural Health Monitoring in Wireless Sensor Networks by the Embedded Goertzel Algorithm*', in, 2011 IEEE/ACM International Conference on Cyber-Physical Systems, use the efficient Goertzel algorithm to compute transmissibility. Lynch, J. P., Sundararajan, A., Law, K. H., et al.: '*Embedding Damage Detection Algorithms in a Wireless Sensing Unit for Operational Power Efficiency*', Smart Materials and Structures, 2004, 13, (4), use an autoregressive process model to fit vibration data to sets of coefficients for different environmental and operational conditions. In some approaches, WSNs are used to perform modal analysis on structures. These approaches have the potential to achieve computational efficiency, however the extent to which they ameliorate the problem of environmental and operational variability is unclear. Also, regarding modal analysis in particular, an accurate synchronization of the motes in a network is required at the onset of data collection. Such an accurate synchronization may be expensive and definitely prohibitive in terms of energy consumption for WSNs requiring very frequent measurements. Also, the expectation of frequent and precise synchronization is normally unrealistic in harsh environments where structures are to be monitored.

Largely as a result of environmental and stimuli-related variability, WSNs have not seen widespread commercial usage in SHM applications. Most deployments have been of an experimental nature.

SUMMARY

Exemplary embodiments of the present disclosure relate to a robust system and method that can be used to address the problem associated with implementing vibration-based SHM for local damage detection in large structures situated in environments with unknown and difficult or impossible-to-control environmental and stimuli-related variability. Also, in contrast to the majority of other methods for structural health monitoring, embodiments of the present disclosure do not require an engineering model of the monitored structure (e.g., there is no need in any part of embodiments of the present disclosure to carry out finite element analysis).

Exemplary embodiments are both computationally efficient and demonstrably effective at circumventing variability due to extraneous factors. As one example, exemplary embodiments of the present disclosure can implement a dynamic pattern matching technique that deals with environmental and stimuli-related variability for vibration-based SHM.

In exemplary embodiments, a WSN with motes (i.e., sensors nodes with limited computational resources which often run on batteries with limited energy) can be distributed throughout the monitored engineering/physical structure. Each mote in the WSN can measure vibrations and can use the measured vibrations to compute the value of a relevant statistical feature, which is used herein to refer to a quantity calculated from the raw measured vibration data. The statistical feature can provide useful information about the measured data as a whole, such as a time domain average of the sensed vibrations. Once a particular mote in the WSN computes a value of the statistical feature, the mote can map the value of the statistical feature into a discrete index value. The motes can share their index values amongst themselves to form tuples, or patterns, of index values. Each such ordered tuple stores the aforementioned averages for a specific sequence of motes that exchange information. The sequences of motes are normally determined at static time. Nevertheless, the sequences of motes can also be configured dynamically during WSN operation, driven by the need to focus on new paths on the structure (e.g., due to sensing new sets of motes that get excited within the same windows of time—this process does not require exact synchronization and may be actually offloaded to another processing unit which is not part of the WSN). The resulting tuples of patterns formed at the motes in the WSN can be checked against a reference list of previously observed 'healthy' patterns stored by the motes. The healthy patterns can indicate that the structure being monitored by the motes in the WSN is healthy (e.g., the motes do not detect any structure damage or deficiencies). The healthy patterns can be determined during a training phase that takes place immediately after the system is installed. Also, the healthy patterns can be updated at run time based on new actual measurements that repeat without leading to catastrophic or unhealthy events (as determined by the WSN or by an offline processing unit that then updates the healthy patterns stored in the motes' memories. If a match is not found at run time for an observed pattern, potential damage is flagged.

As described herein, exemplary embodiments of the present disclosure can use a sensor-based statistical approach to flag conditions that are abnormal with respect to operating conditions observed during a training phase or any subsequent pattern updating phases. If embodiments of the WSN are installed on new construction, a generated flag serves to indicate that the structure is transitioning to an unhealthy state. If embodiments of the WSN are installed on a structure that already has damage, a flag would serve to indicate that the condition of the structure is growing worse. By employing a sensor-based statistical approach, it is possible to achieve: (1) an efficient, computationally simple solution suitable for implementation in a WSN (e.g., the structure does not have to be mathematically modeled and the WSN system does not have to solve equations); (2) a portable solution, independent of structure that is easy to deploy since it does not require detailed knowledge of the structure and its behavior to be modeled mathematically; (3) a solution that does not require the values of involved parameters (e.g., external factors) to be input to the system which is a great advantage since either the parameters and/or their values may be unknown or unpredictable. Exemplary embodiments of the present disclosure are applicable to various physical structures and have many applications. As one non-limiting example, exemplary embodiments of the present disclosure are well suited for structures that carry live loads in a linear fashion, such as pipelines (e.g. water or gas) and railroads.

In accordance with embodiments of the present disclosure, a method for monitoring the health of a structure is disclosed. The method involves a wireless network of motes that sense vibrations and are mechanically coupled to an observed structure, wherein the motes in the wireless network can be grouped and motes in each group collectively observe vibrations on a part of the structure (many groups of such motes may be available to monitor different parts of the structure, the motes in each group are ordered to form a virtual linked list of the linear type, and the groups may be reconfigured) and also involves a sequence of index values transmitted to a mote from at least one other mote in the wireless network of motes. Each index value in the sequence of index values being generated by a different one of the motes based on a measured statistical feature of vibrations in the structure. The method also includes comparing the sequence of index values to stored sequences of index values that are stored by the mote and determining, by the mote, whether the structure is damaged in response to results of comparing the sequence of index values to the stored sequences of index values.

In accordance with embodiments of the present disclosure, a mote in a wireless sensor network of a structural health monitoring system is disclosed. The wireless sensor network includes motes that are configured to be mechanically coupled to a physical structure. The mote includes a computer-readable medium including stored tuples of index values generated during a training phase and/or that are updated during operation, a sensor configured to detect mechanical vibrations on the monitored physical structure, a radiofrequency transceiver; and a controller operatively coupled to the computer-readable medium, the sensor, and the radiofrequency transceiver. The controller is configured to (a) determine whether there is a change in a health of the physical structure based on an index value generated by the controller in response to measured vibration data from the sensor and the stored tuples of index values or (b) determine whether there is a change in the health of the physical structure based on the index value generated by the controller in response to measured vibration data from the sensor, at least one other index value received from at least one preceding mote in the wireless sensor network via the radiofrequency transceiver, and the stored tuples of index values.

In accordance with embodiments of the present disclosure, a structural health monitoring system is disclosed. The structural health monitoring system includes a base station and motes configured to form a wireless sensor network mechanically coupled to a physical structure. For each observed vibration event, all motes in a group collect vibration data. At given times each mote generates a statistical feature value to collectively represent its vibration data observed after the last time it generated a statistical feature value. The first mote in the virtual linked list maps its statistical feature value to an index value. In effect, this value composes a 1-tuple (singleton) of index values. The first mote transmits its 1-tuple to the second mote in the linked list. The second mote appends its own index value to the one received from the first mote, thus forming a 2-tuple of index values. The mote then transmits the 2-tuple to the third mote in the linked list. Similarly, the third mote appends its index value to the 2-tuple to form a 3-tuple, and transmits the 3-tuple to the next mote in the list. This process continues up until the second-to-last mote in the list. The last mote does not transmit a tuple; it only receives a tuple. Using a pattern matching approach, each mote in the group determines whether or not its tuple of index values, which consists of its own index value combined with the index value of any prior motes in the linked list (if there are any), is indicative of a change in the health of the physical structure.

Any combination and/or permutation of embodiments is envisioned. Other objects and features will become apparent from the following detailed description considered in conjunction with the accompanying drawings. It is to be understood, however, that the drawings are designed as an illustration only and not as a definition of the limits of the present disclosure.

BRIEF DESCRIPTION OF THE DRAWINGS

So that those having ordinary skill in the art will have a better understanding of how to make and use the disclosed systems and methods, reference is made to the accompanying figures.

DETAILED DESCRIPTION

Exemplary embodiments of the present disclosure relate to systems and methods for SHM in which a sensor networking including motes distributed with respect to a structure. The sensor network can utilize dynamic pattern matching to monitor local damage in the structure without modeling or solving equations to ascertain or separately account for extraneous factors, such as environmental and stimuli-related variability, which tend to limit the applicability of conventional SHM techniques to experimental use.

Figure 1:
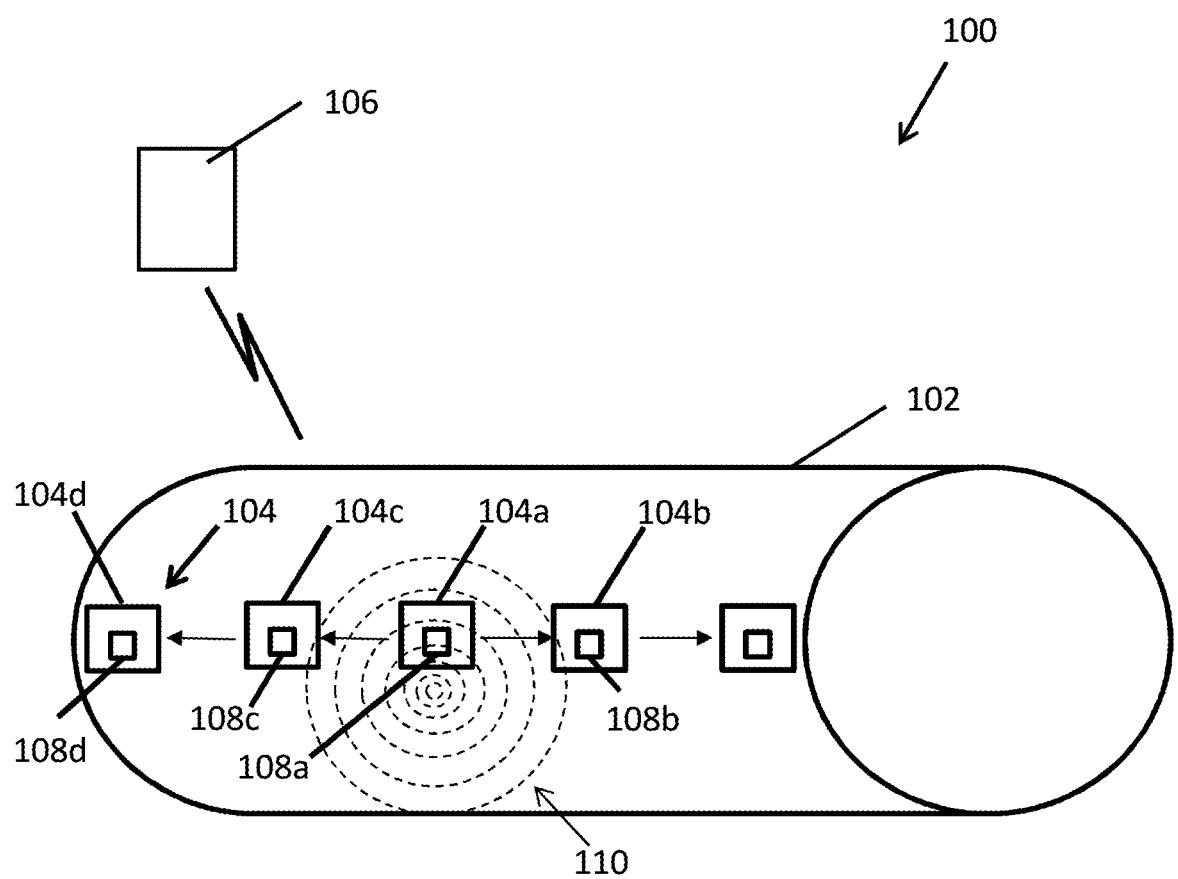
FIG. 1 shows an exemplary embodiment of a structural health monitoring system including wireless sensor network with motes to perform structural health monitoring in accordance with embodiments of the present disclosure.

FIG. 1 depicts an exemplary embodiment of a structural health monitoring system 100 configured to perform vibration-based structural health monitoring (SHM) to detect local damage in an engineering/physical structure 102. The sensor system 100 can include motes 104 that form a sensor network. In exemplary embodiments, the motes 104 can be configured to wirelessly communicate with each other such that the sensor network is a wireless sensor network. The motes 104 can be integrally connected to the structure 102 and can be distributed through the structure 102. One or more stimuli can generate vibrations in the structure 102 that can be detected by one or more of the motes 104. In an operational phase, the motes 104 can measure the vibrations as the vibrations vibrate through the structure 102. Each mote 104 that senses the vibration generated by the stimuli can generate a statistical feature value based on the measured vibration data, and each mote 104 that generates the statistical feature value can correlate the statistical feature value with an index value.

The motes 104 share their index values with other motes to form tuples. For example, after one of the motes 104 senses vibrations and establishes an index value for the vibration, the mote can broadcast the index value for consumption by other motes within the transmission range of the mote and/or according to a specified transmission chain (e.g., transmission between motes can form a chain utilizing a ring topology). The mote(s) that receive the broadcasted index value (or the mote intended to be the recipient of the broadcast) may have also established its/their own index values based on sensing the vibrations and can append their index value to the index value received from the broadcast to form a set, tuple, or pattern of index values, which can be compared against stored sets, tuple, or patterns of index values. If the set, tuple, or pattern of index values do not match one of the stored sets, tuples, or patterns of index values, one or more of the motes 104 wirelessly transmit a flag to indicate that the structure's health has deteriorated. In exemplary embodiments, one or more of the motes 104 can transmit the flag to an external base station 106 that is monitoring the sensor network and the base station 106 can generate notifications or alerts associated with the health of the structure.

As a non-limiting example, as shown in FIG. 1, a vibration source can generate a vibration 110 in the structure 102. As the vibration 110 propagates through the structure, the motes 104 can sense the vibration 110. For example, the mote 104a can be closest to the origin of the vibration 110 and can sense the vibration 110 before the other motes. The mote 104a can process sensed vibrations (e.g., measured data relating to the vibration) and can generate a statistical feature value based on the measured data. Subsequently, the mote 104a can correlate or map the generated statistical feature value to an index value. After establishing the index value $v_A$, the mote 104a can compare the index value $v_A$ against stored sets, tuples, or patterns 108a of index values to determine whether the index value $v_A$ corresponds to one of the stored sets, tuples, or patterns 108a.

The mote 104a can also transmit the index value $v_A$ (as a broadcast message) to one or more other motes in the wireless sensor network. For example, the transmission of the index value from the mote 104a can be received by motes 104b and/or 104c. The motes 104b and/or 104c can also sense the vibration 110 as it propagates through the structure 102, and each of the motes 104b and 104c can establish their own index value for the sensed vibration in a similar manner as the mote 104a (e.g., $v_B$ and $v_C$, respectively). When the motes 104b and/or 104c receive the index value $v_A$ from the mote 104a, the motes 104b and 104c can append their own index values ($v_B$ and $v_C$, respectively) with the index value $v_A$ from the mote 104a such that the mote 104b creates a set, tuple, or pattern of index values that includes $v_A$ and $v_B$ and the mote 104c creates a set, tuple, or pattern of index values that includes $v_A$ and $v_C$. The mote 104b can compare the created set, tuple, or pattern of index values against stored sets, tuples, or patterns 108b of index values to determine whether one of the stored sets, tuples, or patterns 108b corresponds to the set, tuple, or pattern ($v_A$, $v_B$). Likewise, the mote 104c can compare the created set, tuple, or pattern of index values against stored sets, tuples, or patterns 108b of index values to determine whether the one of the stored sets, tuples, or patterns 108b corresponds to the set, tuple, or pattern ($v_A$, $v_C$).

If the sets, tuples, or patterns of index values created by each of the motes 104a-c match their corresponding stored sets, tuples, or patterns 108a-c of index values, respectively, the motes 104a-c determine that there has been no noticeable change in the health of the structure 102. In some embodiments, the motes 104a-c can create log to store this determination with a time stamp (e.g., a day and time that the determination was made) to generate a health record for the structure 102 and/or can transmit the determination, indirectly or directly, to the base station 106 (which may maintain a log).

If the sets, tuples, or patterns of index values created by one or more of the motes 104a-c do not match one of their corresponding stored sets, tuples, or patterns 108a-c of index values, respectively, the mote(s) can generate a flag to indicate that the structures health has deteriorated and can transmit the flag, indirectly or directly, to the base station 106. For example, the motes 104a and 104b may match their created set, tuple, or pattern of index values indicating that there is not noticeable change in the health of the structure 102, while the mote 104c may be unable to match the created set, tuple, or pattern $(v_A, v_C)$ to the stored sets, tuples, or patterns 108c. As a result, the mote 104c can generate a flag to indicate that it detected a change in the health of the structure 102. In some embodiments, the mote 104c can create log to store this determination with a time stamp (e.g., a day and time that the determination was made) to generate a health record for the structure 102 and/or can transmit the determination, indirectly or directly, to the base station 106 (which may maintain a log and/or generate a notification or alert).

After the motes 104b and 104c create their sets, tuples, or patterns $(V_A, V_B)$ and $(V_A, v_C)$, respectively, the motes 104b and 104c can each broadcast the created sets, tuples, or patterns, and such broadcasts can be received by other motes in the system, which can in turn, generate index values, append their index values on to the received sets, tuples, or patterns to create their own, new sets, tuples, or patterns; and compare the newly created sets, tuples, or patterns of index values against their stored sets, tuples, or patterns of index values. For example, the mote 104d can receive a broadcast from the mote 104c that includes the set, tuple, or pattern $(v_A, v_C)$ and can generate its own index value $v_D$ in response to sensing the vibration 110. The mote 104d can append the index value to the set, tuple, or pattern $(v_A, v_C)$ to create a new set, tuple, or pattern $(v_A, v_C, v_D)$ and this newly created set, tuple, or pattern can be compared against stored sets, tuples, or patterns 108d stored by the mote 104d.

In exemplary embodiments, the index values and the order of the index values in the created sets, tuples, or patterns can be compared against the index values and the order of the index values in the stored sets, tuples, or patterns. In such embodiments, if either the index value or the order of the index values in the created sets, tuples, or patterns do not match the stored sets, patterns, or tuples, it can be determined by the motes that there has been a change to the health of the structure 102. Thus, even if a stored set, tuple, or pattern includes each of the index values of a created set, tuple, or pattern, it can be determined that a match exists if the order of the index values in the stored set, tuple, or pattern differs from the order of the index values from the create set, tuple, or pattern.

In some embodiments, each of the motes 104 in the system 100 can have a unique identifier, and the motes 104 can send their unique identifier with the index values and/or their created sets, tuples, or patterns such that the motes receiving the broadcast can associate each of the index values with a corresponding one of the motes and/or determine whether they should process the broadcast. In some embodiments, the broadcast message can include the identifier of the mote for which the message is intended. In such embodiments, in addition to matching the index values and the order of the index values in a created set, tuple, or pattern against a stored set, tuple, or pattern, the motes can be configured to require that the index values, the motes that establish the index value, and the order of the index value match the index values, the identity of the motes associated with the index values, and the order of the index values in stored sets, tuples, or patterns.

The stored sets, tuples, or patterns can be generated by each of the motes 104 during a training phase (e.g., when the motes are installed in the structure or any time thereafter). As one example, the base station 106 can receive measured vibration data and/or statistical feature values from the motes in response to vibrations, and the base station 106 can generate a database of sets, tuples, or patterns of index values to be distributed to the motes. In exemplary embodiments, the portions of the databases can be distributed to different motes. As another example, a series of vibrations can be generated in the structure and the motes can build the sets, tuples, or patterns in an identical manner as when attempt to determine whether there is a noticeable change in the health of the structure. Each set, tuple, or pattern generated during the training period can be stored by the motes for use after the training period to detect deteriorations in the health of the structure 102.

As described herein, exemplary embodiments of the health monitoring system 100 can use a sensor-based statistical approach to flag conditions that are abnormal with respect to operating conditions observed during a training phase. If embodiments of the system 100 are installed on new construction, a flag serves to indicate that the structure is transitioning to an unhealthy state. If embodiments of the system 100 are installed on a structure that already has damage, a flag would serve to indicate that the condition of the structure is growing worse.

By employing a sensor-based statistical approach as described herein, it is possible to achieve: (1) an efficient, computationally simple solution suitable for implementation in a WSN (e.g., the structure does not have to be mathematically modeled and the WSN system does not have to solve equations); (2) a portable solution, independent of structure that is easy to deploy; (3) a solution that does not require the values of involved parameters (e.g., external factors) to be input to the system. Exemplary embodiments of the present disclosure are applicable to various physical structures and have many applications. As one non-limiting example, exemplary embodiments of the present disclosure are well suited for structures that carry live loads in a linear fashion, such as pipelines (e.g. water or gas) and railroads.

While the illustrative example shown in FIG. 1 shows a one-dimensional linear array of motes, exemplary embodiments of the sensor system can include two-dimensional and/or three-dimensional arrays of motes electrically and integrally connected to a structure such that communications between the one or more motes can follow a single path or multiple paths and transmission paths can extend in a single direction or multiple directions.

Figure 2:
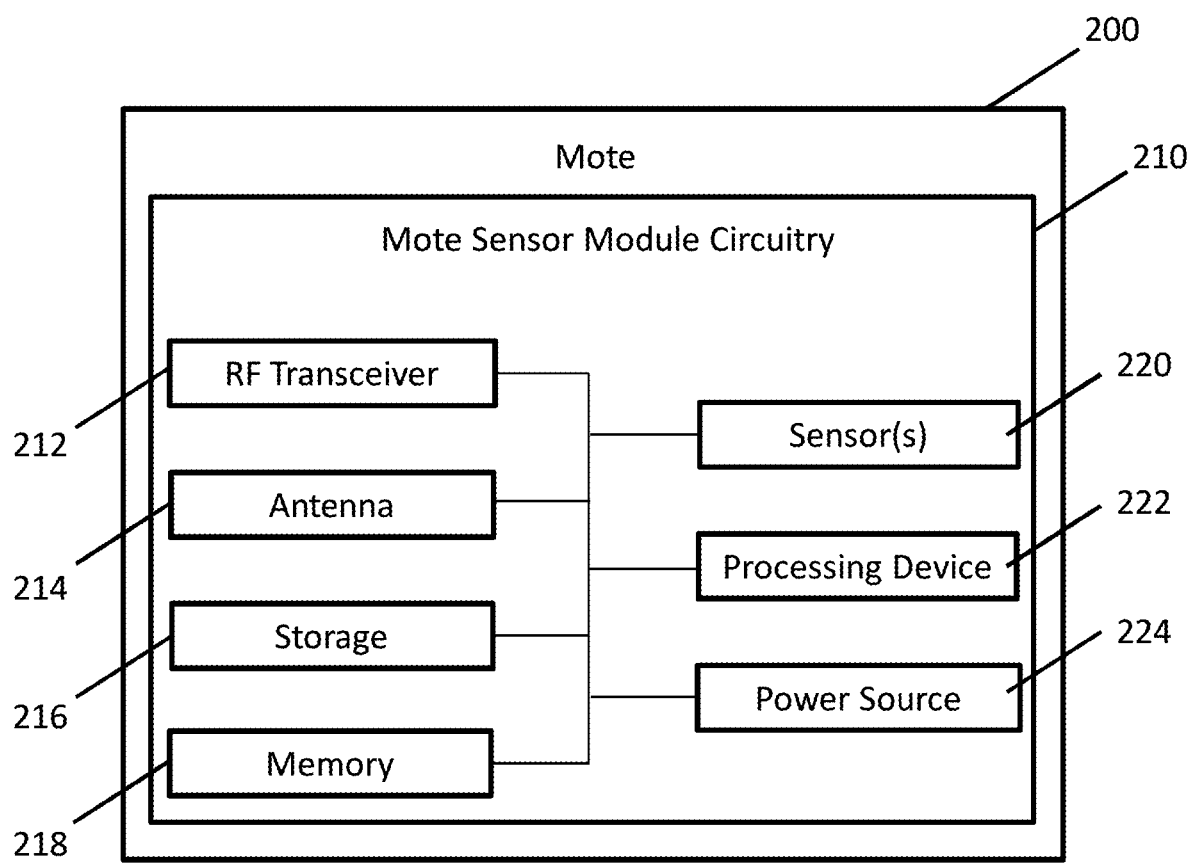
FIG. 2 shows a block diagram of an exemplary embodiment of the mote sensor module circuitry in accordance with embodiments of the present disclosure.

FIG. 2 is a block diagram depicting the sensor module circuitry 210 for a mote 200 (e.g., an embodiment of the motes 104). The circuitry 210 can include a radio frequency (RF) transceiver 212, an antenna 214, storage 216, memory 218 (e.g., RAM), sensor(s) 220, a processing device or controller 222, and a power source 224.

The RF transceiver 212 can be configured to transmit (e.g., via a transmitter of the RF transceiver) and/or receive (e.g., via a receiver of the RF transceiver) wireless transmissions via an antenna 214. For example, the RF transceiver 212 can be configured to transmit one or more messages, directly or indirectly, to one or more other motes and/or to a base station and/or to receive one or more messages, directly or indirectly, from one or more other motes and/or the base station. The RF transceiver 212 can be configured to transmit and/or receive messages having at a specified frequency and/or according to a specified sequence and/or packet arrangement. As one example, the RF transceiver 212 can utilize the Contiki Rime protocol. As another example, the RF transceiver can be a BlueTooth® transceiver configured to conform to a BlueTooth® wireless standard for transmitting and/or receiving short-wavelength radio transmissions typically in the frequency range of approximately 2.4 gigahertz (GHz) to approximately 2.48 GHz. As another example, the RF transceiver 212 can be a Wi-Fi transceiver (e.g., as defined IEEE 802.11 standards), which may operate in an identical or similar frequency range as BlueTooth®, but with higher power transmissions. Some other types of RF transceivers 212 that can be implemented by the sensor module circuitry 210 includes RF transceivers configured to transmit and/or receive transmissions according to the Zigbee® communication protocol, and/or any other suitable communication protocol.

The storage device 216 can include any suitable, non-transitory computer-readable storage medium, e.g., read-only memory (ROM), erasable programmable ROM (EPROM), electrically-erasable programmable ROM (EEPROM), flash memory, and the like. In exemplary embodiments, the storage device 216 can store firmware, which can be embodied as computer-readable/executable program code stored on the non-transitory computer-readable storage device 216 and implemented using any suitable, high or low level computing language and/or platform, such as, e.g., Java, C, C++, C #, assembly code, machine readable language, and the like.

The memory 218 can include any suitable volatile or non-volatile non-transitory computer-readable storage medium (e.g., random access memory (RAM), such as, e.g., static RAM (SRAM), dynamic RAM (DRAM), and the like). In some embodiments, the data/information and/or executable code for implementing the firmware can be retrieved from the storage device 216 and copied to memory 218 during and/or upon implementation of the structural health monitoring processes described herein. Once the data/information has be used, updated, modified, replaced, and the like, the data/information may be copied from memory 218 to the storage device 216.

The sensor(s) 220 can be configured to measure vibrations propagation through a structure (e.g., the structure 102). The sensor(s) 220 can be configured to measure vibrations based on one or more sensed parameters including, for example, displacement, velocity and acceleration resulting from the vibrations. As a non-limiting example, the sensor(s) 220 can be formed of a piezoelectric material that converts the mechanical vibrations into corresponding electrical signals. In an example embodiment, the sensor(s) can be implemented as accelerometers. The electrical signals can be output from the sensor(s) 220 to the processing device or controller 222 for processing.

The processing device 222 can include any suitable single- or multiple-core microprocessor. The processing device 222 can be programmed and/or configured to execute firmware to implement one or more structural health monitoring processes and communicate (e.g., via the RF transceiver 212) information corresponding to the one or more structural health monitoring processes to other motes and/or the base station. The processing device 22 can retrieve information/data from, and store information/data to, the storage device 216 and/or memory 218. For example, vibration measurements by the sensor(s) 220; statistical feature values generated based on the vibration measurements; established index values; sets, tuples, or patterns of index values; and/or any other suitable information/data for implementing the firmware and/or that may be used by the firmware may be stored on the storage device 216 and/or a memory 218.

The power source 224 can be implemented as a battery or capacitive elements configured to store an electric charge. In some embodiments, the battery may be replaceable. As another example, in some embodiments, the power source 224 can be a rechargeable power source, such as a battery or one or more capacitive elements configured to be recharged via a connection to an external power supply, via induction, and/or to be recharged by an energy harvesting device, such as photovoltaic or solar cells and/or any other suitable energy harvesting devices.

As described herein, each of the motes in the wireless sensor network are configured (e.g., via the firmware) to measure vibrations (e.g., via the sensor(s) 220) and use the measured vibration data to calculate a statistical feature value (e.g., via the controller 222). Overall, it can be advantageous to use the simplest feature possible to impose as little computational burden as possible on the motes (e.g., to conserve power and computing resources). In exemplary embodiments, the motes can use time-domain statistical features, such as the average absolute deviation (AAD) feature. While an exemplary embodiment can utilize the AAD feature, exemplary embodiment can utilize other statistical feature as exemplary embodiments of the present disclosure do not depend upon using an exclusive statistical feature; rather, any feature, subject to the constraint that it must be sensitive to damage, can be used. The general formula for computing AAD can be seen in Eq. 1. In the equation '$a_b$' is the value, at a particular instant in time, of the parameter being measured, '$a_M$' is a DC offset, and 'T' is the total number of samples over which the average is to be performed.

$$AAD = \frac{1}{T}\sum_{b=1}^{T} |a_b - a_M|. \qquad \text{Eq 1}$$

The computation of AAD requires relatively little energy, as it can be computed primarily in an online fashion and involves only simple operations. It is also of substantial use as it is sensitive to many different types of structural damage. As one non-limiting example, AAD is sensitive to corrosion: that is, the gradual wearing-away of structural material. When an element of a structure corrodes it loses thickness, and as such its elastic properties change. In general, as thickness decreases, the elastic modulus, which is defined as stress per unit strain, decreases; that is, it takes less stress, which is defined to be force per unit area, to produce the same strain in the element. Given this, for a particular vibration inducing-stimulus, the amplitude of the vibrations in structure increase as corrosion sets in. As such, the AAD of the vibrations can increase in response to the increase in the amplitude of the vibrations.

The AAD feature is sensitive not only to damage (corrosion and other forms) but also to extraneous factors. Temperature, for instance, can change the elastic properties of structural elements and thus the amplitude of their vibrations for a given stimulus. Changes in the intensity of the stimulus producing the vibrations can also change the intensity of the vibrations and thus the value of the AAD feature. For instance, in the case of a railroad bridge, the intensity of vibrations in the bridge deck at a location over which the train is moving will increase with train weight.

In exemplary embodiments, a group of N motes can be distributed about a particular structure in accordance with embodiments of the present disclosure. Each mote measures vibrations and calculates the AAD of the measured vibration data. As such, there is an AAD random variable associated with each mote. The AAD random variables are denoted '$x_i$' herein, where 'i' is the number of the mote (to identify which mote calculated the AAD random variable). The set of AAD random variables may be expressed as a vector, as seen in Eq. 2.

$$x = \begin{bmatrix} x_1 \\ x_2 \\ \vdots \\ x_N \end{bmatrix}. \quad \text{Eq 2}$$

The AAD random variables in the 'x' vector can be correlated. That is, it can be assumed that none of the elements of the covariance matrix associated with the 'x' vector are equal to zero. This is a valid assumption in many cases, and is especially true when the motes are in spatial proximity to each other. The elements of the covariance matrix can be found using Eq. 3.

$$C_{i,j} = \text{cov}(x_i, x_j) \quad \text{Eq 3.}$$

When the structure is healthy, the 'x' random variables follow a particular probability distribution. The probability density function (PDF) for this distribution will be denoted $p_h(x)$. There is a good chance, for instance, that the random variables will follow (at least approximately) a multivariate Gaussian distribution. The PDF for an arbitrary multivariate Gaussian distribution can be seen in Eq. 4. In the equation 'it' is the mean vector corresponding to the 'x' vector.

$$p_g(x) = \frac{1}{2\pi^{N/2}\sqrt{\det(C)}} \exp\left(-\frac{1}{2}(x-\mu)^T C^{-1}(x-\mu)\right). \quad \text{Eq 4}$$

Figure 3:
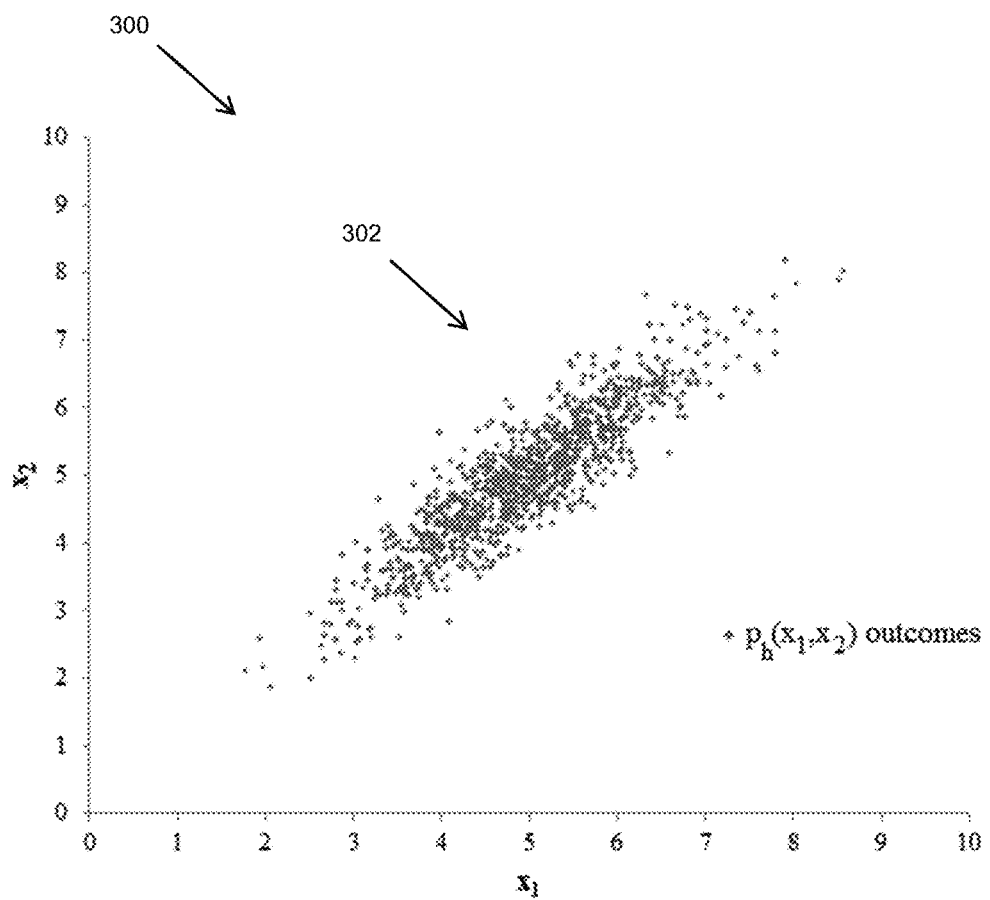
FIG. 3 shows a graph illustrating outcomes from a sample healthy distribution for an example two mote system in accordance with embodiments of the present disclosure.

FIG. 3 shows a graph 300 illustrating outcomes 302 from a sample healthy distribution for an exemplary two mote system, where $p_h(x)=p_g(x)$, $x=[x_1,x_2]$. The x-axis corresponds to AAD random variable $x_1$ and the y-axis corresponds to AAD random variable $x_2$. The graph includes one thousand (1000) outcomes 302. Note the dense concentration of outcomes 302 in the middle of the graph 300, where $p_h(x_1, x_2)=p_g(x_1,x_2)$. For $p_g(x_1,x_2)$, the following values is used for the mean vector: $\mu=[\mu_1=5, \mu_2=5]$, and the covariance matrix is as follows: $C=[1, 0.9; 0.9, 1]$.

For a general 'x' vector, the set of N AAD random variables of the vector can be mapped into an N-dimensional space, where a point is identified as an N-tuple consisting of the values of the N random variables. For instance in FIG. 3, the random variables $x_1$ and $x_2$ are mapped into a two dimensional space. Here a point is identified as a 2-tuple consisting of the values of the random variables as follows: $(x_1, x_2)$.

Figure 4:
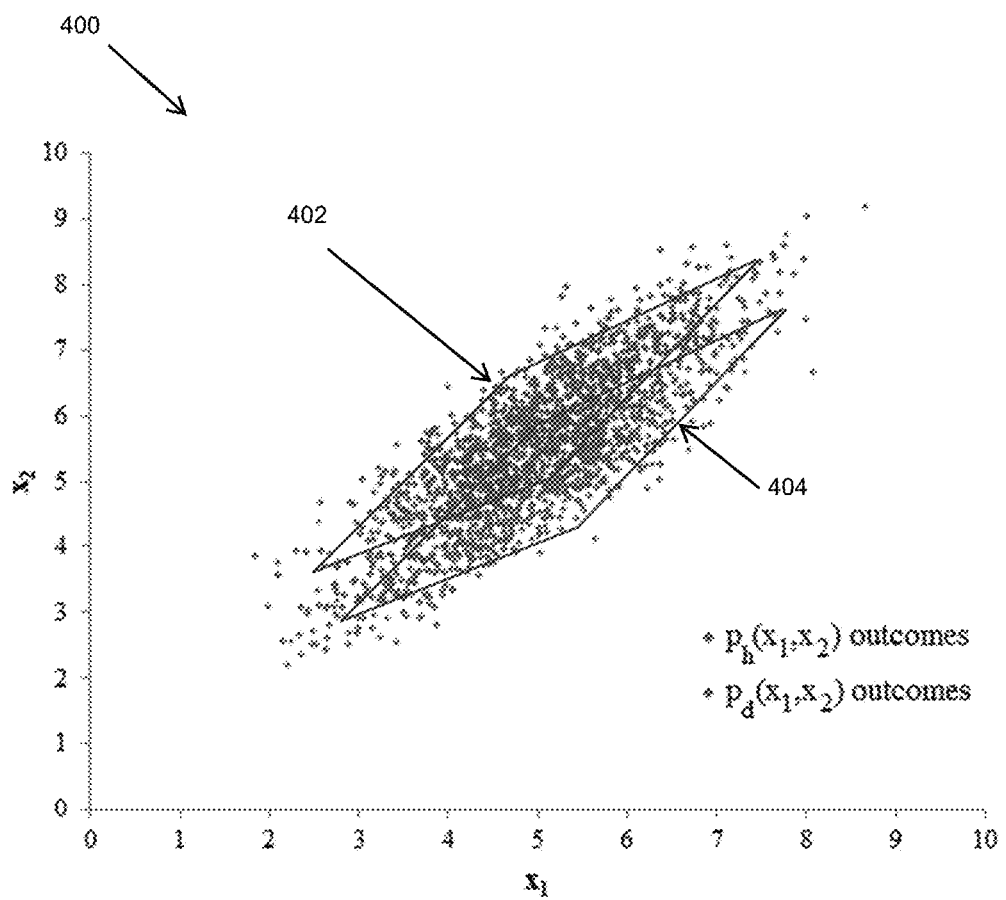
FIG. 4 shows a graph illustrating outcomes from the distribution of FIG. 3 in comparison to outcomes from a sample damage distribution in accordance with embodiments of the present disclosure.

For correlated random variables, the outcomes of a healthy distribution will generally fall within a particular region of the N-dimensional space formed by the N random variables. This region is denoted as 'S' herein. This is exemplified in FIG. 3 where the outcomes 302 of $p_h(x_1,x_2)$ are concentrated toward the middle of the plot. When damage occurs around one of the N motes, the distribution shifts, as shown in FIG. 4, which shows a graph 400 with outcomes 402 corresponding to $p_d(x_1,x_2)$ and outcomes 404 corresponding to $p_h(x_1,x_2)$. The x-axis corresponds to AAD random variable $x_1$ and the y-axis corresponds to AAD random variable $x_2$. The distribution that results is denoted as $p_d(x)$ herein. When the distribution shifts as a result of damage to the structure being monitored by the motes, the outcomes 402 occur outside of the region 'S' more frequently than with the healthy distribution, $p_h(x)$. This is illustrated in FIG. 4, where the damage outcomes were generated by shifting the mean of the $x_2$ random variable as follows: $p_d(x_1,x_2)=p_h(x_1,x_2+c)$, $c=1$.

Embodiments of the structural health monitoring system divides the N-dimensional space associated with the N AAD random variables into N-dimensional blocks. This can be done by each mote by mapping the values of each random variable $x_i$ into a discrete set of index values (e.g., by the motes). In doing so, an index value random variable is created by each mote for each $x_i$ variable. The index value random variables may be expressed as a vector, as seen in Eq. 5. One way to map the $x_i$ variables into index value variables is to use the floor function, as seen in Eq. 6. The mapping can be performed in a linear fashion, with a linear function $g(x)$, as seen in Eq. 7.

$$v = \begin{bmatrix} v_1 \\ v_2 \\ \vdots \\ v_N \end{bmatrix}. \quad \text{Eq 5}$$

$$v_i = \lfloor g_i(x_i) \rfloor. \quad \text{Eq 6}$$

$$v_i = \left\lfloor \frac{x_i}{Y} \right\rfloor. \quad \text{Eq 7}$$

The N-dimensional space associated with the N $v_i$ random variables is a discrete mapping of the continuous N-dimensional space associated with the N AAD random variables. The space associated with the $v_i$ variables consists of blocks of points from the AAD variable space indexed by N-tuples, or patterns, of index values.

Figure 5:
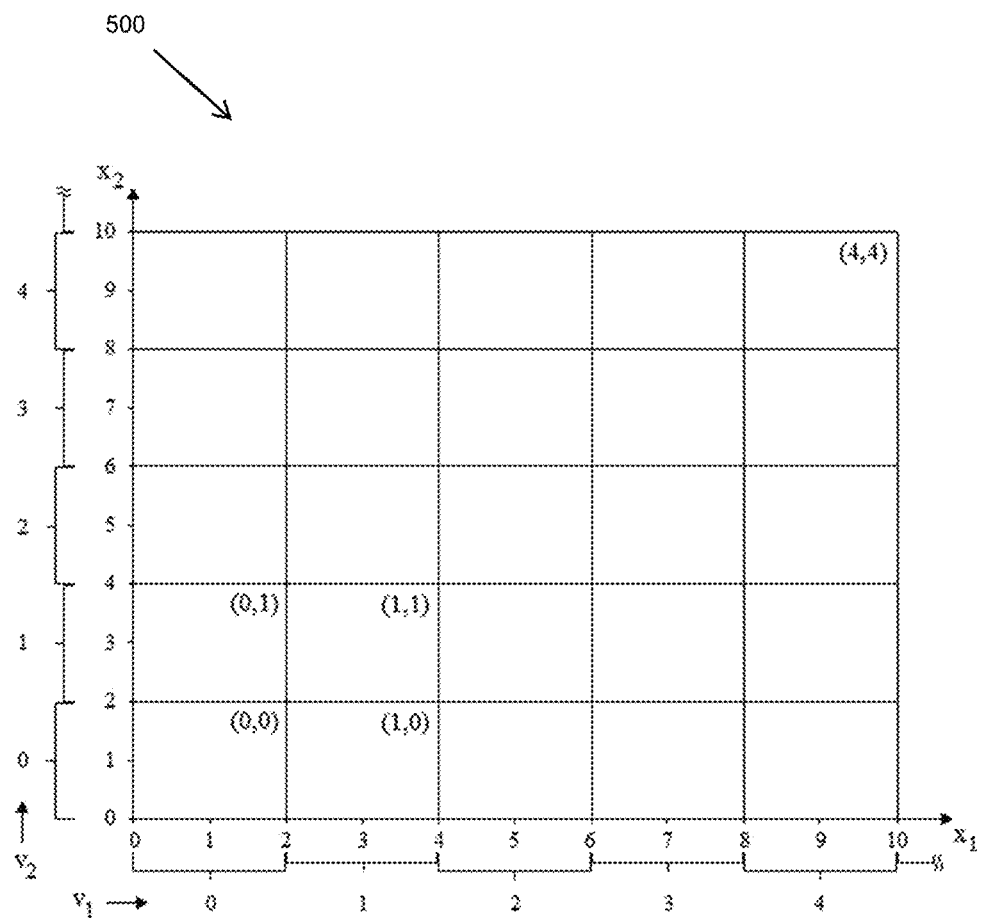
FIG. 5 shows an illustration of the discretization of space associated with average absolute deviation AAD (representing an example statistical feature) random variables for an example two mote system in accordance with embodiments of the present disclosure.

FIG. 5 is a graph 500 illustrating mapping AAD random variables to index values for an illustrative two mote structural health monitoring system in accordance with embodiments of the present disclosure. In FIG. 5, the variables $x_1$ and $x_2$ calculated by the first mote and the second mote, respectively, are mapped into $v_1$ and $v_2$, respectively, using Eq. 7 with Y=2. For example, the x-axis shows the mapping of the AAD random variable $x_1$ to the index values $v_1$ and the y-axis shows the mapping of the AAD random variable $x_2$ to the index values $v_2$. Each block of points is indexed by a 2-tuple consisting of the values of $v_1$ and $v_2$. Examples of 2-tuples appear in parentheses within several of the blocks. They are formatted as follows: $(v_1, v_2)$.

As described herein, exemplary embodiments of the structural health monitoring system includes two primary phases: a training phase and an operational phase. During the training phase, the N motes obtain a number of data points in response to vibrations in the structure, where each data point consists of an AAD value from each one of the motes. To generate a data point each mote collects vibration data, calculates the AAD of the data, and sends its AAD value to a base station (e.g., base station 106 shown in FIG. 1). The timing of the data collection between the motes depends upon the application and is arranged to achieve as high a correlation between the AAD random variables as possible. Once the base station collects all of the AAD values for a particular data point, it takes each mote's AAD value and determines the corresponding index value using each mote's mapping function, $g_i(x_i)$ (Eq. 6.). It combines the index values to form an N-tuple of index values and thus determines which block the data point falls into. It then stores the N-tuple in memory. The base station collects many data points during the training phase, and thus, builds a large database of N-tuples corresponding to the healthy structure; thereby, in terms of blocks, establishing the healthy behavior of the structure.

Figure 6:
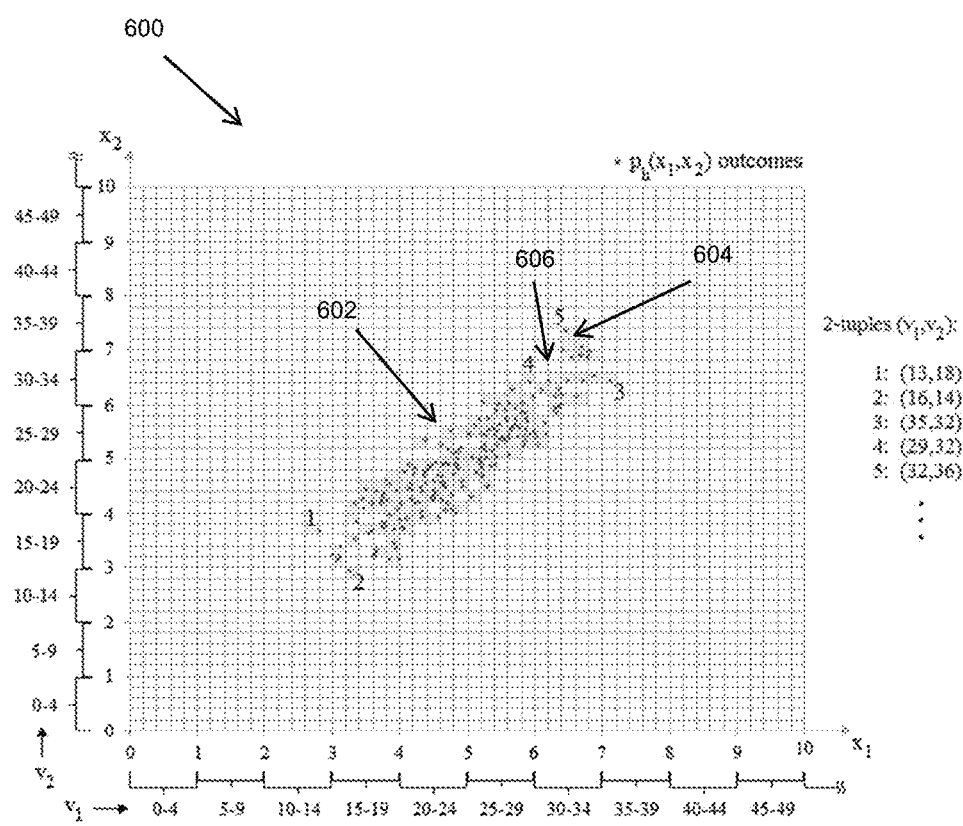
FIG. 6 shows an illustration of the training phase process for an example two mote system in accordance with embodiments of the present disclosure.

An illustration of the training process for a two mote system in accordance with embodiments of the present disclosure can be seen in FIG. 6, which shows a graph 600 including outcomes 602 from a healthy distribution and blocks 604 within which the outcomes 602 of the healthy distribution fall. The PDF for the healthy distribution, $p_h(x_1, x_2)$, is the same distribution referred to in FIG. 3. The AAD variables $x_1$ and $x_2$ were mapped into $v_1$ and $v_2$ using Eq. 7 with Y=0.2.

From the N-tuple database for the N motes, subset databases can be obtained for subsets of the motes. For example, with continued reference to FIG. 6, a database of 1-tuples can be generated for the mote associated with the $x_1$ random variable by simply deleting the $v_2$ values from the entries of the 2-tuple database. This can be used to implement the operational phase of embodiments of the structural health monitoring system in a distributed manner. During the operational phase, to assess the condition of a structure, the motes (in the aggregate) collect a data point, determine which block it falls into, and then determine whether or not the corresponding N-tuple is one recorded by the base station during the training phase. If it is not, damage is indicated. To accomplish this in a distributed fashion, among the N motes a transmission chain can be defined. Each mote can be assigned to a particular link in the chain. The N motes can be denoted '$m_1$' through '$m_N$'. Mote $m_1$ is defined to be the first mote in the transmission chain, and mote $m_N$ is defined to be the last mote in the transmission train. Each mote contains a subset of the base station's N-tuple database that corresponds to the subset of motes consisting of itself and each of its predecessors in the transmission chain.

Since embodiments of the structural health monitoring system can collects a finite amount of training data, the system may not be able to record all of the tuples that are indicative of a healthy structure (recall that tuples represent N-dimensional blocks). With specific reference to FIG. 6, the blocks 604 are blocks in which data points fall during the training phase. These blocks, which correspond to 2-tuples, are recorded as healthy problems. In some instances, there may be blocks 606 dispersed between the blocks 604, as is the case in FIG. 6, for which no data points fell during the training phase. The blocks 606 typically represent a healthy structure and would likely be recorded if more training data was gathered. Since not all of the tuples that are indicative of a healthy structure are recorded, there can be a risk of false positives. For instance, it is possible for the system to report damage when none exists.

To mitigate the risk of false positives, exemplary embodiments of the structural health monitoring system can employ a process during the training phase wherein the blocks that are likely to be indicative of a healthy structure are recorded, even if no data points observed during the training phase fall within those blocks. As described herein, data points from a healthy structure generally fall within a particular region of the N-dimensional space (e.g., the region denoted by 'S'). Since embodiments of the system can collect a finite amount of training data, the region 'S' can be approximated. The approximation of the region 'S' is referred to herein as a 'bounded region.'

Figure 7:
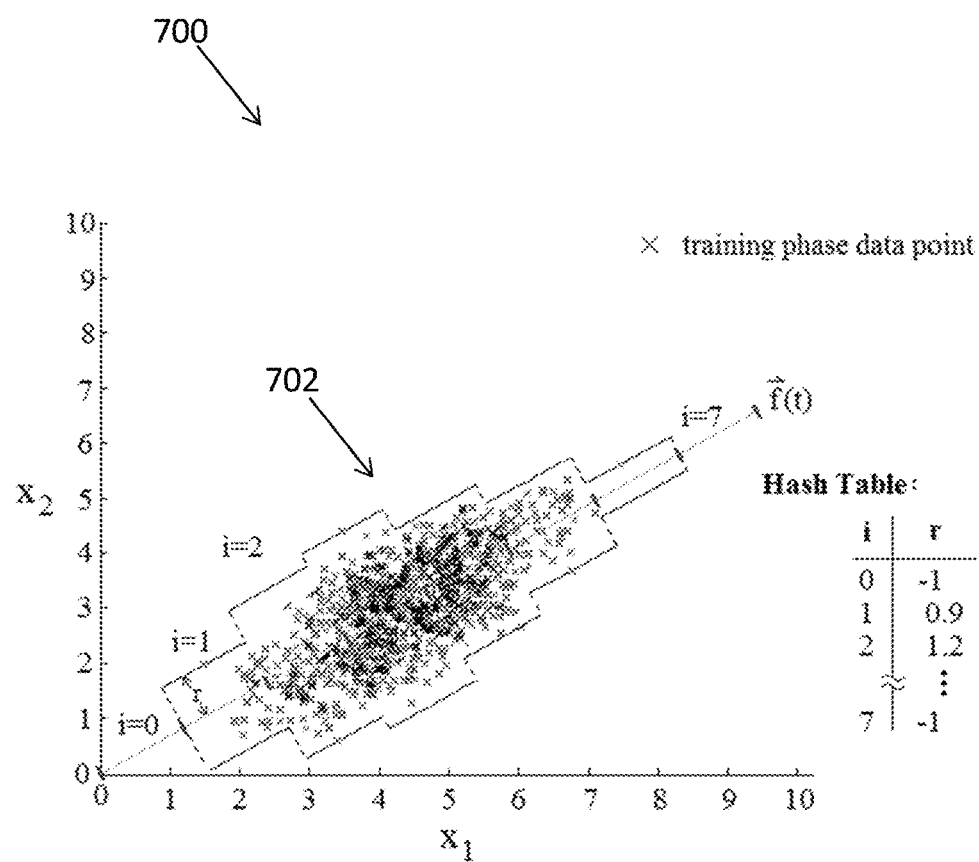
FIG. 7 shows a process of establishing a bounded region for an example two mote system in accordance with embodiments of the present disclosure.

The process of establishing a bounded region 702 for an example two mote system in accordance with embodiments of the present disclosure is illustrated in FIG. 7, which shows a graph 700. To begin, a line ($\bar{f}(t)$) is fit to the data points obtained during the training phase. The line will be described by the vector-valued function of Eq. 8 and the position along $\bar{f}(t)$ is defined according to Eq. 9. Position p(t) will be divided into a set of hash keys using Eq. 10.

$$\bar{f}(t) = \langle x_1(t), x_2(t), \ldots, x_N(t) \rangle \quad \text{Eq. 8}$$
$$= \langle x_{1,0}, x_{2,0}, \ldots, x_{N,0} \rangle + t\langle d_1, d_2, \ldots, d_N \rangle.$$

$$p(t) = \sqrt{(x_1(t) - x_{1,0})^2 + (x_2(t) - x_{2,0})^2 + \ldots + (x_N(t) - x_{N,0})^2}. \quad \text{Eq 9}$$

$$r = \lfloor Kp(t) \rfloor. \quad \text{Eq 10}$$

Each hash key can have a single value associated with it; the hash key value will be denoted by 'r'. Each of the hash key values can be initialized to −1. For each data point gathered during the training phase, exemplary embodiments of the structural health monitoring system can determine the location ($x_{1,p}$, $x_{2,p}$, . . . , $x_{N,p}$) on $\bar{f}(t)$, for which the Euclidean distance between the data point and $\bar{f}(t)$ is minimum. Then, the minimum Euclidean distance itself can be calculated. The position of ($x_{1,p}$, $x_{2,p}$, . . . , $x_{N,p}$) on $\bar{f}(t)$ can then be determined using Eq. 9. Upon completion, Eq. 10 can be used to determine the hash key associated with the position value. The hash key can be used to retrieve the associated position value. The calculated Euclidean distance can then be compared to the retrieved value. If the Euclidean distance exceeds the retrieved value, Euclidean distance replaces the value in the database. This process will be repeated for many data points.

After the process of generating the bounded region is complete, the values for the hash keys for which there are no data points remain set to −1. As a result, the value associated with a particular hash key can define the boundary of the part of the bounded region associated with that hash key. The more data points that are taken into consideration, the more closely the bounded region will resemble 'S'. Accuracy can also be increased by increasing the K value in Eq. 10, wherein K determines how many intervals (has keys) position p(t) is split into. Once the bounded region is established, the bounded region can be used to determine which N-dimensional blocks fall within the bounded region.

Pseudocode corresponding to the firmware executed by each mote for the operational phase algorithm can be seen in below. In the pseudocode, variables with overbars are vectors. For each data point, each mote collects vibration data, calculates the AAD of the data, and then maps the AAD value to an index value using its designated mapping function, $g_i(x_i)$. These operations correspond to lines 8 through 10 in the pseudocode. The mote then combines its index value with those of any predecessors in the transmission chain to form a tuple of index values, and checks the tuple against those in its database to determine if it is present. This process corresponds to lines 11 through 18 in the pseudocode. If the tuple is not present, the mote immediately sends an alert to the base station indicating that damage might be present. The action taken by the mote based upon whether or not it finds the tuple in its database is represented by lines 19 through 25 in the pseudocode. In the pseudocode, one iteration of the while loop corresponds to one data point. It should be noted that, assuming no damage is detected, the base station does not have to do any processing. In the operational phase, the role of the base station can be to process alerts from the motes when the motes detect an abnormal condition (a change in the health of the structure being monitored). For instance, the base station might relay an alert over the internet to the engineering office in charge of the structure on which the system is installed.

Pseudocode Algorithm for Operational Phase

```
1:    i = index of link in transmission chain
2:    N = number of motes in the system (as defined earlier)
3:    m_i = mote with link index i
4:    D_i = database for mote m_i
5:    tuple = pattern of index values (as defined earlier)
6:    while TRUE
7:        for i = 1:N
8:            data = collect_vibration_data( );
9:            AAD = (1/T)Σ_{b=1}^{T} |data(b) – a_M|   // from Eq. 1
10:           index_value = ⌊g_i(AAD)⌋;    //from Eq. 6
11:           if i = 1
12:               tuple = index_value;
13:               result = check_D_i_for_tuple(tuple);
14:           else
15:               received = wait_for_tuple_from_ m_{i-1}( );
16:               tuple = concatenate_tuples(index_value, received);
17:               result = check_D_i_for_tuple(tuple);
18:           end
19:           if result = FOUND
20:               if i < N
21:                   transmit_tuple_to_m_{i+1}(tuple);
22:               end
23:               else
24:                   transmit_alert_to_base_station( );
25:               end
26:           end
27:           wait_for_stimulus( );
28:       end
```

When monitoring an entire structure, with motes distributed throughout the structure, it is unlikely that all of the associated AAD random variables will be strongly correlated with each other. In this case, the motes can be divided into several highly correlated N-mote groups. Here, a cluster topology can be implemented, where each cluster independently runs an instance of an embodiments of the structural health monitoring system (e.g., a single structure can includes several subsystems of motes, where each subsystem independently monitors the health of a portion of the structure). In general, the motes in each cluster can be connected using a ring topology, although exemplary embodiments can utilize other topologies (e.g., a star topology, a tree topology, etc.). During the training phase a cluster head can be elected.

In another exemplary embodiment, exemplary embodiments of the structural health monitoring system can change the configuration of the clusters to account for correlational changes between the vibrations (e.g., caused by wear and tear). For example, exemplary embodiments of the structural health system can periodically gather (e.g., via the base station) a number of statistical feature values from each of the motes in the wireless sensor network during the operational phase, and can use the data to determine (e.g., via the base station) if the correlation patterns have changed. If correlation has changed, the clusters can be reconfigured accordingly.

The operational phase of the algorithm is to be implemented in a distributed fashion, on the network's motes. As described, each of the motes must check a tuple obtained through measurement against a reference list of healthy tuples. In the pseudocode, this process is represented by the 'check_D_i_for_tuple' function. Assuming that, during the training phase, the base station sorts the lists of healthy tuples before storing them on the motes, the process of checking a list of healthy tuples for a measured tuple amounts to searching a sorted array. As such, the 'check_D_i_for_tuple' function can be implemented with a binary search algorithm. On any given mote, the binary search algorithm has a worst-case run time of $\lceil \log_2(p_i+1) \rceil$, where $p_i$ is the size of the list of healthy tuples on mote $m_i$ (the size of $D_i$). Since $p_i$ tends to increase exponentially as 'i' increases, the worst-case run time for each individual mote increases as 'i' increases. The worst case run-time for the algorithm of the pseudocode as a whole is equal to the sum of the worst-case run times for the individual motes, as seen in Eq. 11.

$$T = \sum_{i=1}^{N} \lceil \log_2(p_i + 1) \rceil. \quad \text{Eq 11}$$

By making some simplifying assumptions, a closed form solution to the worst-case run time for the algorithm of the pseudocode can be determined. Firstly, if each value of '$p_i$' is a power of two, the worst-case run time for a given mote is given by $\log_2(p_i)$. The '$p_i$' values can be made to be powers of two by padding the $D_i$ databases. Secondly, it should be assumed that '$p_i$' increases with 'i' in the manner seen in Eq. 12. This can be achieved (at least approximately) in most cases by using Eq. 6 such to realize Eq. 12. That is, subject to other constraints to be introduced shortly, blocks can be generated using Eq. 6 such to make Eq. 12 true. Given these assumptions the worst case run time for the algorithm of the pseudocode can be found from Eq. 13.

$$p_i = p_1^i. \quad \text{Eq 12}$$

$$T = \sum_{i=1}^{N} \log_2(p_1^i) \quad \text{Eq 13}$$

$$= \log_2(p_1) \sum_{i=1}^{N} i$$

$$= \frac{\log_2(p_1)}{2}(N)(N+1).$$

In Eq. 10, it can be seen that the worst-case run time of the algorithm grows quadratically with the number of motes in the structural health monitoring system. As such, in terms of 'N', the worst case performance of the algorithm may be expressed as $O(N^2)$. It can also be seen from Eq. 13 that the run time increases logarithmically with '$p_1$'. In terms of '$p_1$' the worst case performance of the system can be expressed as $O(\log(p_1))$.

Overall, the performance of the algorithm decreases as the number of motes in the system increases. It also decreases as the number of healthy tuples increases. One way to optimize performance is to keep the number of tuples as small as possible. This can be done by using non-linear mapping functions (non-linear $g_1(x_i)$) for the motes. The idea is to achieve large blocks in the space where $p_h(x)$ has its highest density (the space 'S') and smaller blocks elsewhere. This helps to reduce the number of blocks and thus the number of healthy tuples. To do this, each mapping function $g_i(x_i)$ should be developed based upon the marginal PDF of the random variable that it is mapping. In particular, in terms of the value of the random variable being mapped, the minimum value of the derivative of the mapping function, $g_i'(x_i)$, should correspond to the maximum value of the PDF. This is the case because one wants to achieve the fewest index values per AAD value (largest blocks) where the random variable has its highest density. As the PDF decreases on either side of its maximum value, the value of the derivative of the mapping function should increase.

Figure 8:
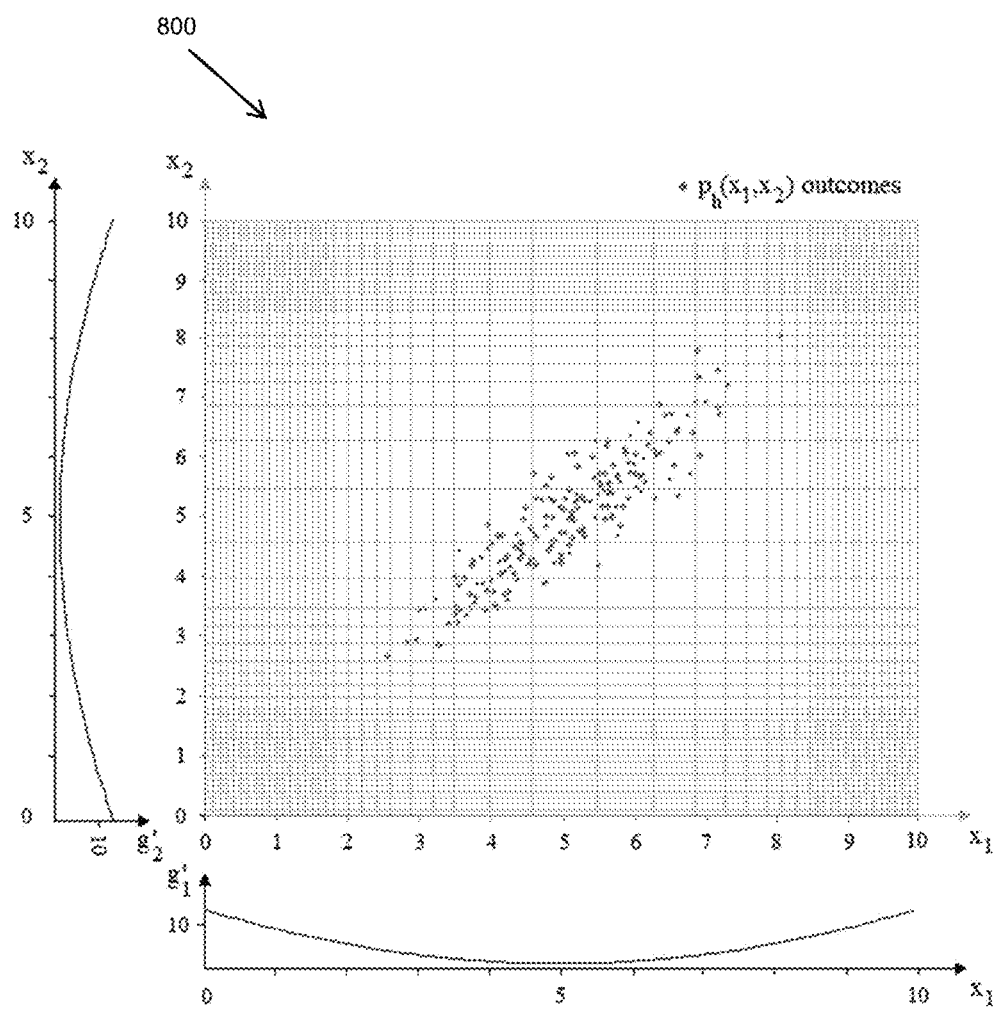
FIG. 8 shows an illustration of blocks obtained through non-linear mapping for a two mote system.

An illustration of blocks obtained through non-linear mapping for a two mote system can be seen in FIG. 8. For the system the healthy distribution used for FIGS. 3, 4, and 6 is used. Recall that a bivariate Gaussian PDF was used for $p_h(x_1, x_2)$: $p_h(x_1, x_2) = (x_1, x_2)$. With a multivariate Gaussian PDF, the marginal PDF for each random variable is a Gaussian distribution. As such, graphically speaking, for each random variable '$x_i$' a concave function centered about the variable's mean should be used for the derivative of the mapping function. The simplest function to use here is a quadratic function of the form seen in Eq. 14. In this equation, the constants 'm' and 's' are used to tune the mapping function to achieve an appropriate block size. The corresponding mapping function (the integral of $g_i'(x_i)$) can be seen in Eq. 15. In Eq. 15, the value of 'c' is determined based upon the constraint that $v_i = 0$ ('0' index value) should correspond to $x_i = 0$ ('0' AAD value): $g_i(x_i = 0) = 0$.

$$g_i'(x_i) = \frac{(x_i - \mu_i)^2}{m} + s, \qquad \text{Eq 14}$$

$$g_i(x_i) = \frac{(x_i - \mu_i)^3}{3m} + sx + c, \quad c = \frac{\mu_i^3}{3m}. \qquad \text{Eq 15}$$

To generate the blocks shown in graph 800 of FIG. 8, Eq. 15 was used to map the AAD random variables into index value random variables. In particular, the following values were used for 'm' and 's' for both $g_1(x_1)$ and $g_2(x_2)$: m=2, s=1. From $p_g(x_1, x_2)$, $\mu_1$ and $\mu_2$ were both equal to five. In FIG. 8, vertical lines indicate index values associated with $x_1$ and horizontal lines indicate index values associated with $x_2$.

Using MATLAB, for the two mote system of FIG. 8, random variables $x_1$ and $x_2$ were mapped into index values using Eq. 12, using m=2 and s=1. Vertical lines indicate index values associated with $x_1$ and horizontal lines indicate index values associated with $x_2$. The derivatives of the mapping functions are shown next to the two axes. Note that block size gets larger as the derivatives approach their minimum values, where the distribution of outcomes is the densest. A calculation was performed to show the effect of 'm' on the number of tuples recorded during the training phase. Here, there was first generated 200 sample outcomes of $p_g(x_1, x_2)$. Based upon the outcomes, the number of tuples that would be recorded if the system were to use linear mapping, as described by Eq. 7 was then determined. Here, Y=0.2 was used. Then, also based upon the outcomes, the number of tuples was determined that would be recorded if the system were to use non-linear mapping using Eq. 15, for several different values of 'm.' Here, s=1 was used. The results of the calculations are summarized in Table 1.

TABLE 1

Number of tuples for several different values of 'm' for the two mote system of FIG. 8. The number of tuples for a linear mapping with Y = 0.2 is also shown.

| | Mapping Technique | | | | | |
|---|---|---|---|---|---|---|
| | Linear, Y = 0.2 | Quadratic, m = 0.1 | Quadratic, m = 0.5 | Quadratic, m = 1 | Quadratic, m = 1.5 | Quadratic, m = 2 |
| Number of Tuples | 112 | 81 | 52 | 37 | 29 | 25 |

The results of Table 1 show that the number of tuples that must be stored decreases as 'm' gets larger. This is because, as 'm' is made larger, block size is being strategically increased in the areas where the distribution of outcomes is the most dense. The reduction in tuples comes at a cost, however. In general, when using non-linear mapping, there is a tradeoff between accuracy and memory/energy consumption. As blocks are made bigger, the number of tuples that must be stored in memory decreases. Additionally, the amount of energy that the motes must spend searching their databases, on average, decreases. However, the potential for false negatives increases. That is, it becomes more likely that a data point from a damaged structure (one that falls outside of the region 'S') will fall inside a healthy block and thus go undetected. Accuracy can be improved by decreasing block size and/or generating a bounded region as described herein. As block size approaches zero, the likelihood that a data point outside of the region 'S' will fall inside a healthy block also approaches zero. Accuracy, in this regard, approaches 100%.

Zolertia's Z1 mote was used to implement simulations and an experimental embodiment of the health monitoring system in accordance with the present disclosure. The Z1 mote is a general purpose development platform for WSNs, and is compatible with the popular Tmote family of motes. According to Zolertia, the Z1 offers roughly a two times improvement in performance over the Tmote motes.

One possible operating system to use for an embodiment of the health monitoring system is Contiki, which is the operating system used for the experimental embodiment of the structural health monitoring system and simulations. Contiki is a lightweight, open-source operating system designed for use in WSNs, and is based on an event-driven kernel, where preemptive multithreading is implemented as an application library that can be linked to programs that require it. As a result, it combines the advantages of event-driven systems and systems that use multi-threading.

There are many applications for embodiments of the structural health monitoring system of the present disclosure. One such application is that of railroad monitoring. This potential application was investigated in detail through experimentation and simulation. For the experiments, a model railroad setup was used. This allowed extraneous factors (such as train weight, track temperature, and train speed) and structural condition to be carefully controlled.

Figure 11:
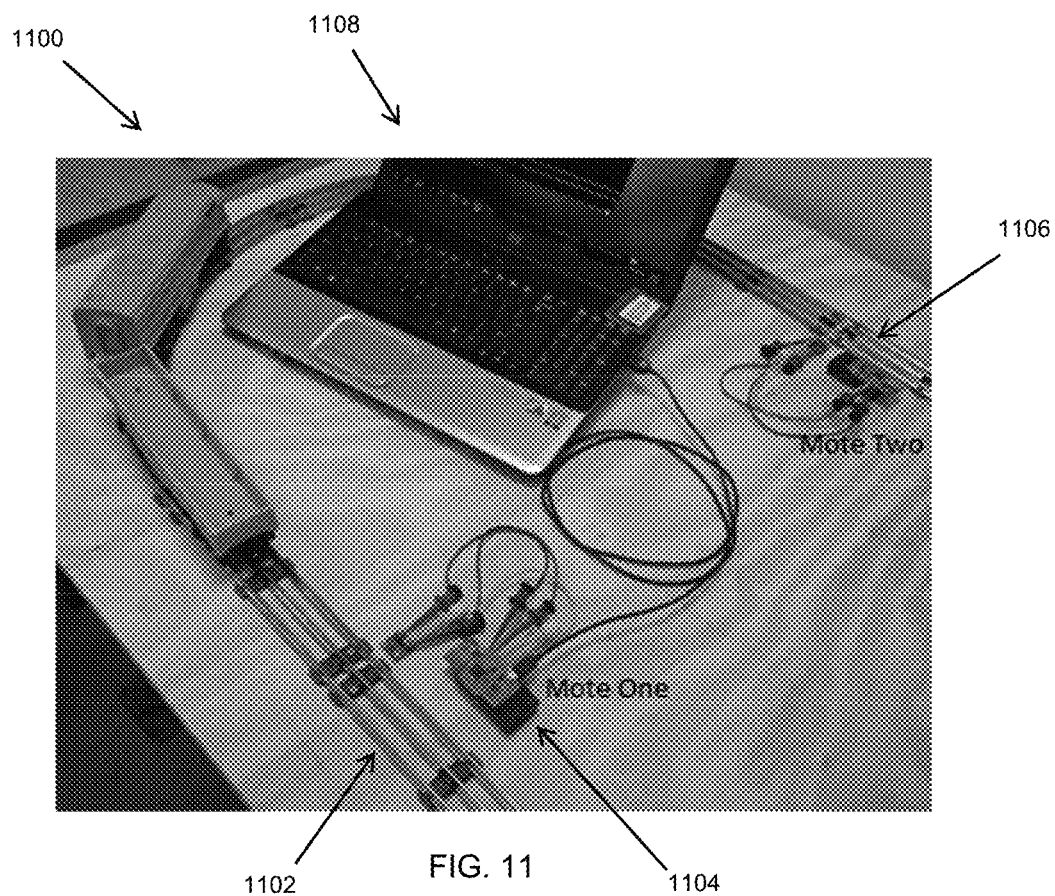
FIG. 11 shows an experimental implementation of an embodiment of the structural health monitoring system in accordance with embodiments of the present disclosure.

Importantly, the results obtained from the model setup provide insight into the behavior of full-scale systems. An image of the setup can be seen in FIG. 11. For the simulations, a network simulator, Cooja, that was designed to simulate WSNs whose motes run the Contiki operating system was used. In Cooja, a simulated Contiki mote is an actual compiled and executing Contiki system, compiled for a specific hardware platform.

Simulations were performed to investigate the improvement in efficiency garnered by implementing an experimental embodiment of the structural health monitoring system with a distributed architecture, using the algorithm of the pseudocode described herein, over a centralized architecture in a railroad monitoring application. To measure energy in the simulations, Contiki's Powertrace application (a power state tracking mechanism) was used.

Figure 9:
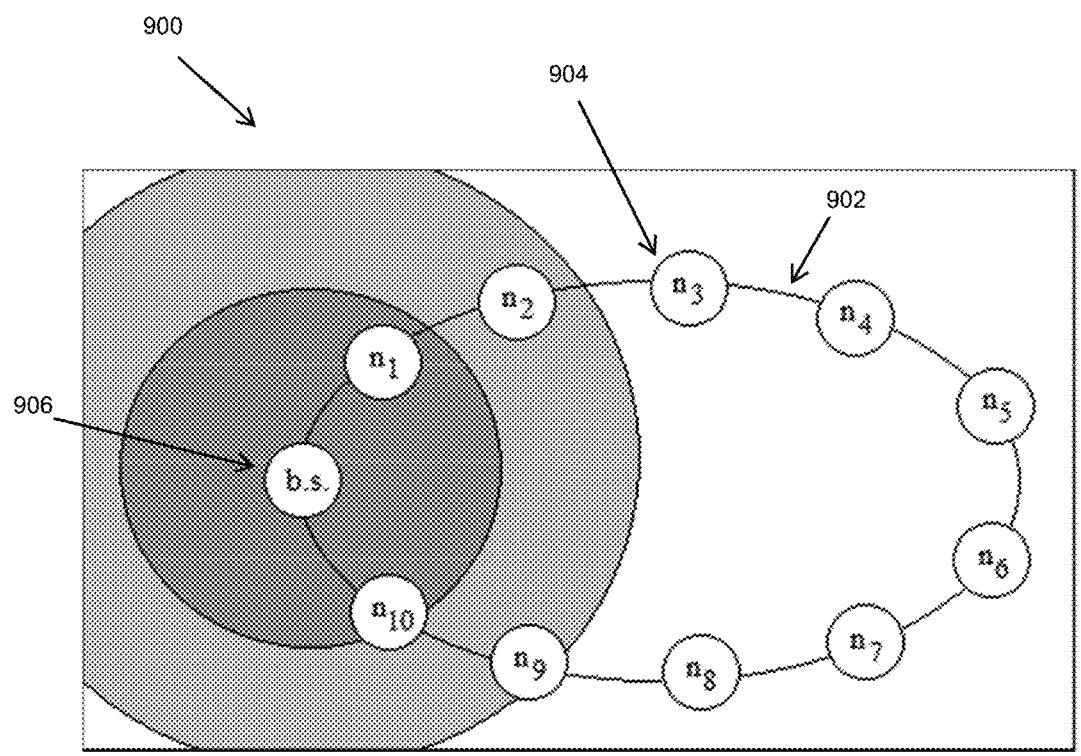
FIG. 9 shows an illustration of the system used in the energy consumption simulations.

Overall, two simulations were performed. For both simulations, an example system 900 with ten motes 904 and a base station 906 was used. The motes 904 and base station 906 were placed along a virtual, closed railroad track 902 as shown in FIG. 9. A virtual train was made to move around the track in a clockwise fashion, starting and ending at the base station. As the train passed over the motes, the motes were made to collect simulated vibration data. Regarding transmissions, each node (including the base station) had only enough power to reach its immediate neighbors. The inner circle surrounding the base station, which has a radius of 50 m, indicates the size of the area over which the base station and motes can reliably transmit Contiki's Rime protocol stack was used for wireless communication.

In the first simulation, a centralized architecture was implemented in which all of the processing was done by the base station. As the train passed over each mote, each mote was made to collect vibration data and immediately transmit the raw data to the base station. Since the nodes only had enough power to transmit to their two nearest neighbors, multi-hop communications were necessary. Here, a shortest path routing protocol was used.

In the second simulation, a distributed architecture was used. The algorithm of the pseudocode described herein was implemented on the motes. As the train passed over each mote, the mote was made to collect vibration data, calculate the AAD of the data, and determine the corresponding index value. The mote was then made to combine its index value with those from any previous motes to form a tuple and search for the tuple in its database. Assuming no damage was found, the mote would then send its index value and those from previous motes on to the next mote in the transmission chain (the next mote in the direction of the movement of the train).

Figure 10:
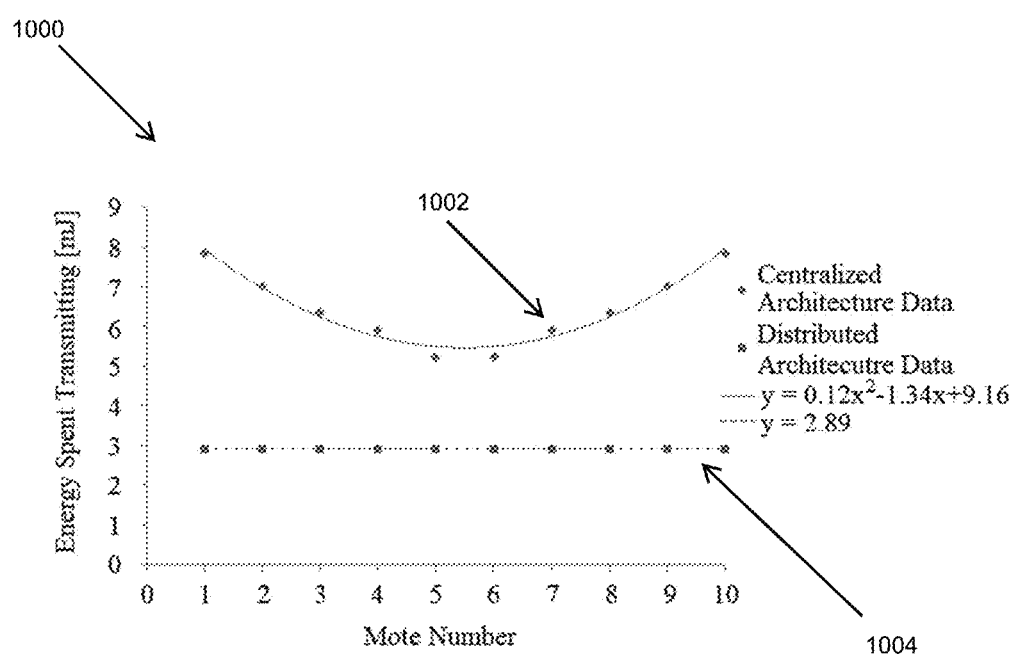
FIG. 10 shows a graph of energy spent transmitting versus mote number for local and distributed processing.

In each simulation, the amount of energy that each mote spent on transmitting was measured. FIG. 10 shows graph 1000 including data obtained through the simulation. The x-axis corresponds the motes and the y-axis corresponds to the energy dissipated for transmissions in milli-Joules. The curve 1002 corresponds to a centralize architecture in which the base station performs the analysis and the curve 1004 corresponds to a distributed architecture in which each mote performs the analysis. The curves 1002 and 1004 shown in FIG. 10 are fits to the data determined using MATLAB. The mote numbers correspond to the motes 904 shown in FIG. 9. The discrete points represent the data obtained from the simulations.

As shown in FIG. 10, when the vibration data is processed locally (e.g., at each mote), all of the motes spend the same amount of energy transmitting. This is because the number of transmissions per mote and the amount of data per transmission are the same for each mote. It can also be seen that when the vibration data is processed by the base station, each mote spends substantially more energy transmitting than it does in the case when processing is done on the individual motes.

Recall that in the simulation for the centralized architecture, a shortest path routing algorithm was used. Referring again to FIG. 9, this means that motes $n_1$ through $n_5$ transmit counterclockwise through the network to the base station, and that motes $n_6$ through $n_{10}$ transmit clockwise through the network to the base station. As a result of this, motes $n_1$ and $n_{10}$ had to forward the most packets. This means that they also had to spend the most energy transmitting. Motes $n_2$ and $n_9$ had to forward the second most amount of packets, and thus had to spend the second most amount of energy transmitting. In general, the number of packets that a mote must forward, and the amount of energy that a mote must spend transmitting, decreases as one moves away from the base station. This is why the graph for the centralized architecture, as seen in FIG. 10, is concave.

It should be noted that, although motes $n_5$ and $n_6$ only have their own data to transmit and no packets to forward in the centralized architecture, they still spend more energy transmitting than they do when processing is done locally. This is because, when the data is processed by the base station, the motes have to send more data per transmission than they do when processing is done in a distributed fashion. When the data is processed on the motes, it is compressed into a smaller representative form before it is transmitted. On average, with the distributed architecture, the motes used 50% less energy transmitting than they did with the centralized architecture. The results from the simulations regarding the accuracy of the simulated system were in close accordance with the system's theoretical accuracy. For sufficiently small sub-range sizes, 100% accuracy is attainable. This is at the expense of increased memory and energy consumption.

An experimental embodiment of the health monitoring system was tested on a model railroad setup. The system consisted of two motes 1104 and 1106 and a base station 1108 disposed with respect to model rail tracks 1102. The two motes 1104 and 1006 were modified versions of Zolertia's Z1 mote and the base station 1108 was a PC. The Z1 mote was modified by adding an analog accelerometer and an external voltage reference. This was done because the digital accelerometer that the Z1 comes with was not capable of sampling fast enough for the application (it could sample at 3.2 kHz whereas the system required 10 kHz) and the supplied voltage reference was not stable enough for our analog-to-digital conversions.

In the experiment, to simulate track damage, fastening elements in the track were loosened. Through preliminary experimentation, it was found that the AAD of the vibrations of the structure supporting the track was sensitive to such damage. As such this is the statistical feature that the motes were made to monitor. The only extraneous factor that was allowed to vary in the experiment was train weight. This factor was also found (through preliminary experimentation) to affect the AAD of the support vibrations. In particular, it was found that the AAD of the vibrations increased linearly with cargo (mass added to the train) weight. The other significant factors, such as train speed and air temperature were held constant.

Regarding the setup (referring to FIG. 11), the mote 1104 was connected to the base station via a USB interface. The mote 1106 wirelessly transmitted to The mote 1104. In the experiment, an engine attached to an empty gondola car was first sent around a healthy track at a speed of 0.18 rev/s. Each of the motes collected vibration data, calculated the AAD of its data, and mapped the AAD value to an index value. Overall, the tuple produced by the two index values was found to be healthy. This was the correct result, as no damage had been done to the track. Next, two weights totaling 3.26 kg were placed in the gondola car and the train was again sent around a healthy track at a speed of 0.18 rev/s. Here, for each of the motes, the vibration levels and their associated index values were higher than they were for the run with the empty gondola car. Again, the system determined that the index values were such to produce a healthy tuple. This was the correct result, as no damage had yet been done to the track. After this, to simulate damage, a couple of screws were taken out of the track by the mote 1104. The weights were taken out of the gondola car and the train was then sent around the track at the same speed as the previous two runs. Here, the mote 1106 responded as it did when the train with the empty gondola car was sent around the track with the screws tightened. The AAD of the vibrations corresponded to the same index value. On the other hand, the vibrations at the mote 1104 changed and the AAD value corresponded to a different index value than it did for the healthy run with the empty gondola car. As a result of this, a tuple other than a healthy tuple was produced and the system was able to detect that damage had occurred.

Although the systems and methods of the present disclosure have been described with reference to exemplary embodiments thereof, the present disclosure is not limited thereby. Indeed, the exemplary embodiments are implementations of the disclosed systems and methods are provided for illustrative and non-limitative purposes. Changes, modifications, enhancements and/or refinements to the disclosed systems and methods may be made without departing from the spirit or scope of the present disclosure. Accordingly, such changes, modifications, enhancements and/or refinements are encompassed within the scope of the present disclosure.

The invention claimed is:

1. A method for monitoring the health of a structure, the method comprising:
   receiving, by a mote in wireless network of motes mechanically coupled to a structure, a sequence of index values from at least one other mote in the wireless network of motes, each index value in the sequence of index values being generated by a different one of the motes based on a measured statistical feature of vibrations in the structure;
   comparing the sequence of index values to stored sequences of index values that are stored by the mote;
   determining, by the mote, whether the structure is damaged in response to results of comparing the sequence of index values to the stored sequences of index values;
   measuring the statistical feature of vibrations by the mote;
   mapping a value of the statistical feature to corresponding index value;
   appending the corresponding index value to the sequence of index values;
   transmitting the sequence of index values to a subsequent mote;
   comparing the sequence of index values to stored sequences of index values that are stored by the subsequent mote; and
   determining, by the subsequent mote, whether the structure is damaged in response to results of comparing the sequence of index values to the stored sequences of index values.

2. The method of claim 1, wherein the corresponding index value is appended to the sequence of index values prior to comparing the sequence of index values to the stored sequences of index values.

3. The method of claim 1, wherein the wireless network of motes includes clusters of motes, the clusters of motes being determined based on a degree to which a response of the motes to vibrations in the structure are correlated.

4. The method of claim 3, wherein the clusters are connected using a ring topology.

5. The method of claim 3, further comprising:
   changing a configuration of the clusters to account for changes to the degree to which the response of the motes to vibrations in the structure are correlated.

6. The method of claim 1, wherein the statistical feature is an average absolute deviation of vibrations in the structure.

7. A method for monitoring the health of a structure, the method comprising:
   receiving, by a mote in wireless network of motes mechanically coupled to a structure, a sequence of index values from at least one other mote in the wireless network of motes, each index value in the sequence of index values being generated by a different one of the motes based on a measured statistical feature of vibrations in the structure;
   comparing the sequence of index values to stored sequences of index values that are stored by the mote;
   determining, by the mote, whether the structure is damaged in response to results of comparing the sequence of index values to the stored sequences of index values;
   wherein the results of comparing the sequence of index values to the stored sequence of index values by the mote results in a failure to match the sequence of index values to the stored sequence of index values, and the mote determines that the structure is damaged in response to the failure.

8. The method of claim 7, further comprises:
   transmitting a message to a base station to communicate that the structure is damaged; and
   generating an alert by the base station.

9. A method for monitoring the health of a structure, the method comprising:
   receiving, by a mote in wireless network of motes mechanically coupled to a structure, a sequence of index values from at least one other mote in the wireless network of motes, each index value in the sequence of index values being generated by a different one of the motes based on a measured statistical feature of vibrations in the structure;
   comparing the sequence of index values to stored sequences of index values that are stored by the mote;
   determining, by the mote, whether the structure is damaged in response to results of comparing the sequence of index values to the stored sequences of index values;
   generating the stored sequences of index values based on a set of training data generated from a response of the motes in the wireless network of motes to mechanical vibrations in the structure; and
   distributing the stored sequences of index values to the motes.

10. The method of claim 9, wherein the sequences of index values are determined to have a probability distribution and the probability distribution corresponds to a region of sequences of index values.

11. The method of claim 10, further comprising:
identifying a first group sequences of index values that are likely to be indicative of a healthy structure based on at least one of the sequences of index values in the group being generated based on the set of training data.

12. The method of claim 11, further comprising:
identifying a second group sequences of index values that are likely to be indicative of a healthy structure when none of the sequences of index values generated based on the training data fall within the second group of sequences of index values in response to determining that the second group of sequences of index values fall within the region.

13. A mote in a wireless sensor network of a structural health monitoring system, the wireless sensor network including a plurality of motes that are configured to be mechanically coupled to a physical structure, the mote comprising:
a computer-readable medium including stored tuples of index values generated during a training phase;
a sensor configured to detect mechanical vibration propagating with the physical structure;
a radiofrequency transceiver; and
a controller operatively coupled to the computer-readable medium, the sensor, and the radiofrequency transceiver, the controller being configured to (a) determine whether there is a change in a health of the physical structure based on an index value generated by the controller in response to measured vibration data from the sensor and the stored tuples of index values or (b) determine whether there is a change in the health of the physical structure based on the index value generated by the controller in response to measured vibration data from the sensor, at least one other index value received from at least one preceding mote in the wireless sensor network via the radiofrequency transceiver, and the stored tuples of index values;
wherein the controller is configured to:
generate the index value by calculating a value for a statistical feature of the measured vibration and mapping the value of the statistical feature to the index value;
append the index value to at least one other index value received from another mote in the wireless sensor network to create a new tuple of index values;
compare the new tuple of index values against the stored tuples of index values; and
determine whether there is a change in the health of the physical structure in response to a failure to match the new tuple of index values to one of the stored tuples of index values.

14. The mote of claim 13, wherein the controller transmits the new tuple of index values via the radiofrequency transceiver to a subsequent mote in the wireless sensor network that is configured to determine whether there is a change in the health of the structure based on the new tuple of index values.

* * * * *